United States Patent [19]

Karube et al.

[11] Patent Number: 5,262,310
[45] Date of Patent: Nov. 16, 1993

[54] ENZYMATIC DECOMPOSITION METHOD OF CHITIN-CONTAINING MATERIALS

[75] Inventors: Isao Karube, Kawasaki; Takashi Morita, Tokyo, both of Japan

[73] Assignees: Akebono Brake Industry Co, Ltd., Tokyo; Akebono Research & Development Center Ltd., Saitama, both of Japan

[21] Appl. No.: 887,701

[22] Filed: May 22, 1992

[30] Foreign Application Priority Data

May 31, 1991 [JP] Japan .................. 3-130021
May 31, 1991 [JP] Japan .................. 3-130022

[51] Int. Cl.$^5$ .............. C12P 19/28; C12P 19/26; C12N 9/36; C12N 9/42
[52] U.S. Cl. .............. 435/85; 435/72; 435/84; 435/101; 435/200; 435/206; 435/209; 536/20
[58] Field of Search .............. 435/84, 72, 85, 200, 435/206, 101, 209; 536/20

[56] References Cited

U.S. PATENT DOCUMENTS

| | | | |
|---|---|---|---|
| 4,077,842 | 3/1978 | Cory | 435/188 |
| 4,536,207 | 8/1985 | McCandliss | 536/20 |
| 4,686,185 | 8/1987 | Wakunaga | 435/85 |

FOREIGN PATENT DOCUMENTS 62-5597 2/1987 Japan .
62-146598 6/1987 Japan .
63-273493 11/1988 Japan .
3-219870 9/1991 Japan .

OTHER PUBLICATIONS

Douzou et al "J. Mol. Biol." (1974) 96, 367–380.
Sharon "Proc Roy Soc" (ser B) 167, 402–415.
Blake et al "Proc Roy Soc" (ser B) 167, 378–388.

*Primary Examiner*—Herbert J. Lilling
*Attorney, Agent, or Firm*—Knobbe Martens Olson & Bear

[57] ABSTRACT

Chitin-containing material is heat-treated in organic solvent or in the solvent with water, and then $\beta$-1, 4 glycoside decomposing enzyme is added for decomposing the chitin-containing material by enzyme reaction. Or, chitin-containing material is ultrasonicated in organic solvent or in the solvent with water, and then chitin-containing material is decomposed by enzyme reaction of $\beta$-1, 4 glycoside decomposing enzyme. Further, chitin-containing material is exposed in the solution containing urea and/or surfactant, and then chitin-containing material is let co-exist with $\beta$-1, 4 glycoside decomposing enzyme under the presence or non-presence of urea and/or surfactant for decomposing chitin-containing material. Or, at the time of exposing chitin-containing material in the solution containing urea and/or surfactant, the solution is heated and the $\beta$-1, 4 glycoside decomposing enzyme is added for decomposing chitin-containing material.

11 Claims, 12 Drawing Sheets

ENZYMATIC DECOMPOSITION METHOD OF CHITIN-CONTAINING MATERIALS

BACKGROUND OF THE INVENTION

This invention relates to an enzymatic decomposition method of chitin-containing materials, and in details supplies the method for decomposing chitin-containing materials efficiently by enzyme reaction.

Chitin is a polysaccharide which exists abundantly in the natural world, and is contained in the shell of the Crustacea such as crabs, shrimps, etc., in the outer frame of insects, and in the cell wall, etc. of a certain molds. Chitin is a long molecule where N-acetylglucosamine is linked by $\beta$-1, 4 glycosidic linkage, and the deacetylation of chitin in the highly concentrated thermo-alkali solution yields chitosan. Chitosan demonstrates high adsorption for metal ion and protein, and is utilized as an agglutination agent or as a carrier in bioreactors, etc. The products made from chitin or chitosan have superior compatibility with living bodies and are also used as sutures for physical operation, artificial skins, etc. Further, it is known that polymers or oligomers, decomposed products of chitin and chitosan, have antibacterial and antitumor activities.

Thus, the substance obtained from chitin is highly valued in the industrial application. Since it is difficult to adjust the degree of decomposition in the prior method of acid hydrolysis for decomposing chitin and chitosan, most of the decomposed products are of low molecular weight. On the other hand, the decomposition method utilizing decomposition enzymes such as chitinase, etc. has advantages in that the degree of decomposition can be easily adjusted due to the mild reaction condition and the variable reaction specificity depending on the kind of enzymes, but has the problem that enzymes already known cannot decompose materials efficiently. Therefore, there is a need for the method which can efficiently hydrolize chitin-containing materials and chitosan-containing materials, and makes it possible to control the degree of decomposition.

SUMMARY OF THE INVENTION

The invention is an enzymatic decomposition method for chitin-containing materials in which, in the method for decomposing chitin-containing materials by performing enzyme reaction with decomposition enzyme present in the solution containing chitin-containing materials, chitin-containing materials are heat-treated in organic solvent or in the solvent with water added hereto, and $\beta$-1, 4 glycosidic decomposition enzyme is utilized. This invention further supplies an enzymatic decomposition method for chitin-containing materials in which, in the method for decomposing chitin-containing materials by performing enzyme reaction with decomposition enzyme present in the solution containing chitin-containing materials, chitin-containing materials are ultrasonicated in organic solvent or in the solvent with water added hereto, and $\beta$-1, 4 glycosidic decomposition enzyme is utilized.

The invention also includes an enzymatic decomposition method for chitin-containing materials in which, in the method for decomposing chitin-containing materials by performing enzyme reaction with decomposition enzyme present in the solution containing chitin-containing materials, there are included both the process to expose chitin-containing materials in the solution containing urea and/or surfactant and the process to make chitin-containing materials coexist with $\beta$-1, 4 glycosidic decomposition enzyme under the presence or non-presence of urea and/or surfactant. This invention further supplies, as another mode, an enzymatic decomposition method for chitin-containing materials in which, in the process of exposing chitin-containing materials in the solution containing urea and/or surfactant described above, the heating operation of the solution is included.

The invention is described in details below.

1. Chitin-containing Materials of this Invention

The chitin-containing materials used in this invention can be obtained mainly from the outer shells of the Crustacea such as crabs, shrimps, krills, etc., and from the cell wall fo the fungi including molds, yeasts, mushrooms, etc. These materials can be utilized as the materials for this invention, for instance, after the calcification by dilute acid and deprotenization by concentrated alkali, and then after washing. The method to efficiently decompose such chitin-containing materials by enzymes is explained below

2. The Invention (1) Organic Solvents Used in this Invention

Chitin has a stable crystal structure by hydrogen bond or hydophobic bond in molecules or among molecules. Accordingly, it is estimated that heat-treating chitin in the hydrophobic solvent or in the solvent with water added hereto will weaken the hydrogen bond or hydrophobic bond and facilitate the action of enzymes for decomposition.

As the organic solvents used for this invention, hydrophobic organic solvents insoluble with water can be used in the form of solvent only or mixed with water. Preferably, the solvent can be heated at the temperature of not less than 70° C. Concretely, the following solvents can be used solely, or in the form of mixtures or mixtures with water: straight-chain hydrocarbons such as hexane, heptane, octane, 2-methyl heptane, 2,2,4-trimethyl heptane, nonane, decane, undecane, dodecane, etc.; circular saturated hydrocarbons such as methyl cyclobutane, cyclohexane, methyl cyclohexane, etc.; aromatic hydrocarbons such as benzene, toluene, o-oxylene, m-xylene, p-xylene, ethyl benzene, cumene, etc.; solvents obtained as oil residue such as ligroin, etc.; halogenated hydrocarbons such as carbon tetrachloride, 1,2-dichloroethane, 1,1,2,2-tetrachloroethane, trichloroethylene, chlorobenzene, 2,6-dichlorobenzene, etc.

When the solvent is used in the form of mixtures with water, it is preferable that the ratio of water is 3-50 vol % since enzyme is likely to lose its activity when the volume of water is very low, and the action of solvent on substrate is lessened when water is excessively present. Among the hydrophobic solvents described above, straight-chain hydrocarbons are preferable and suitable; especially, hexane and dodecane are preferable. Further, dodecane containing 10 vol % water is cited as a preferable mode.

(2) Method of heat-treatment on chitin-containing materials

The heat-treatment on chitin-containing materials can be achieved, for instance, by boiling the materials in the solvents described above. At that time, it is preferable to heat the materials by stirring for the purpose of efficiently destroying crystal structure. The heat-treatment may be achieved by using autoclave after having suspended chitin-containing materials in the solvent. There are no limitations with regard to heating time, but several minutes to several hours or so is sufficient if the temperature of solvent has reached nearly to the boiling point.

(3) Decomposition of chitin by enzyme

Decomposition of chitin-containing materials can be performed by adding decomposition enzyme for enzyme reaction to the suspension of chitin-containing materials which is heat-treated in solvent. It is preferable to perform the reaction by stirring for the purpose of increasing the surface area between organic solvent and water, and further for the purpose of increasing contact frequencies between enzyme and substrate. When the chitin-containing material is in the state of emulsion with the addition of surfactant, it is possible to perform the reaction by standing still (without stirring). Further, the reaction can be performed with stirring under the presence of surfactant.

As the surfactant, the following agents are cited: Triton X-100 (polyoxyethylene (10) octyl phenyl ether), Tween 20 (polyoxyethylene sorbitane monoraulate), etc.

As the decomposition enzyme, $\beta$-1, 4 glycosidic linkage decomposition enzyme is used for cutting $\beta$-1, 4 glycosidic linkage which constitutes chitin. For this purpose, such hydrolysis enzymes are cited as, for instance, lysozyme (Mucopeptide N-acetylmuramyhydrolase, EC 3.2.1.17), chitinase (EC 3.2.1.14), etc which are commercially sold in the market. Among these enzymes, lysozyme is easily obtained and inexpensive. The temperature for enzyme reaction can vary within the range which does not inactivate the enzyme, and it is preferable to perform the reaction within the optimum temperature range for enzyme activity.

Preferable reaction conditions when lysozyme is used as the chitin decomposition enzyme are: 30°–60° C. in temperature, neutral in pH, 0.1–0.6M in the ion strength of buffer, 2–8 (W/V) % in the concentration of enzyme, 2–8 (W/V) % in the concentration of substrate (chitin).

The use of heat-resistant enzyme makes it possible to add the enzyme at the time of heat-treatment on chitin-containing materials and to perform enzyme reaction simultaneously with heat-treatment, which enables one to complete the treatment within a short period of time.

Enzyme reaction can be performed under the condition of dissolving enzyme in solvent, but can also be performed by utilizing the insoluble carriers fixed with enzyme as a bioreacter. The fixation of enzyme can be achieved by the method generally accepted for the fixation of enzyme: the method to include enzyme in the polyacrylamide gel, etc., and the method to make enzyme adsorbed by ion exchange resin.

The decomposition substance produced from chitin-containing material as a result of decomposition reaction can be obtained in the form of concentrated solution by letting the reaction solution stand after the completion of reaction and by concentrating the layer of water separated naturally from the layer of solvent. The purification of decomposed substance can be achieved by liquid chromatography, gel filtration, etc. after having removed remaining solvent by treating with adsorbent of active carbon, etc.

(4) Ultrasonication of chitin-containing material

The ultrasonication in the organic solvent instead of heat-treatment by organic solvents as a pretreatment on chitin-containing material makes the material easily digested by the decomposition enzyme. It is estimated that the crystal structure of chitin is loosened by the ultrasonication in the solvent so as to let enzyme act on the material. Solvents similar to those used for heat-treatment can be employed. In this case, solvents unsuitable for heat-treatment can also be used. Further, both heat-treatment and ultrasonication may be employed concurrently.

(5) Application of this invention

The method of this invention can be applied similarly to the enzymatic decomposition of both chitosan and chitin, in which case Chitosanase, etc., may be used as enzymes. In addition, the method may be applied to polysaccharides such as cellulose, xylan, other hemicellulose, insoluble protein, etc. which are hard to perform enzyme decomposition on efficiently due to their stable three-dimentional structure, and also to such polymer compound as lignin, etc. which are hard to decompose.

3. An Alternative Embodiment of the Invention (1) Pretreatment of chitin-containing material Chitin has a stable crystal structure by hydrogen bond or hydrophobic bond in molecules or among molecules, which is considered to be the cause of preventing chitin decomposition enzyme from working on the chitin. Therefore, chitin is considered to become easily digested when hydrogen bond or hydrophobic bond of chitin is loosened.

The hydrogen bonds can be weakened by utilizing compounds such as urea, glycerol, guanidine, etc. For the purpose of weakening hydrophobic bond, surfactant may be used. Accordingly, it is possible to decompose chitin efficiently by exposing chitin-containing material to the solution of these compounds to destroy the crystal structure of chitin, and then by letting chitin decomposition enzyme act on the material.

However, hydrogen bond and hydrophobic bond are generally considered to be contributing to the maintenance of three-dimentional structure necessitated for the activity expression of enzyme protein. Since there exists a risk that enzyme may be inactivated under the conditions of loosening these bonds, strict conditions are necessitated when letting the compounds described above coexist with enzyme. In case that enzyme reaction is performed after having pre-treated chitin-containing material with the compounds described above and then having removed the compound hereof, it is necessary that the structure of chitin is irreversibly changed. In case that enzyme reaction is performed under the presence of the compound hereof, it is necessary that there exist conditions such as not to inactivate chitin-decomposition enzyme.

As the compounds to satisfy these conditions, there can be cited urea, or surfactants of which HLB (Hydrophile Lipophile Balance) value is 10–20. These may be used concurrently. As the surfactants, those of which HLB value is around 14 are especially preferable; for instance, there can be cited Triton X-100 (polyoxyethylene (10)octyl phenyl ether, HLB value-13.5).

For pre-treating chitin-containing material with these compounds, chitin is added to the solution containing these compounds solely or combined, then left to stand for 1–24 hours. It is preferable to stir the solution at that time, but the solution may be left to stand without stirring.

In case that the enzyme reaction is performed in the presence of urea, it is preferable to set the concentration of urea at 0.1–0.4M. When the concentration is too low, the effect of denaturation by urea is little; when the concentration is too high, enzyme is inactivated. Therefore, it is preferable to set the concentration at the range described above. In case that enzyme reaction is performed after having denatured chitin by urea, and then having removed the urea, the urea can be used up to the saturation concentration. In this case, higher concentration is preferred. It is preferable to set the concentration of Triton X-100 at 0.1-5 (W/V) %.

At the time of exposing chitin-containing material to the solution of urea and/or surfactant, heating can accelerate the effectiveness of destroying the crystal structure. Especially, this effectiveness is remarkable when the concentration of urea is low, around 0.1M. It is enough to perform this heat treatment for several minutes to several hours at 100° C., preferably for 30 minutes or so. Chitin-containing material is added to the solution of urea and/or surfactant, which is boiled.

(2) Decomposition of chitin-containing material by chitin-decomposition enzyme.

As the chitin-decomposition enzyme used for this invention, $\beta$-1, 4 glycosidic linkage decomposition enzyme is used to cut $\beta$-1, 4 glycosidic linkage which constitutes chitin. As the enzyme for this purpose, for instance, such hydrolysis enzymes as lysozyme may be used (Mucopeptide N-acetylmuramy-hydrolase, EC 3.2.1.17), etc. Among these, egg white lysozyme is easily obtained and inexpensive. Several origins for chitinase are known, and chitinases originated from Serratia marcescens, *Streptomyces griseus*, etc. are commercially sold in the market.

The method for decomposing chitin-containing material by this invention is described below. Chitin-containing material is added to the solution in which urea and/or surfactant are/is dissolved in buffer. After this or after heating this solution, chitin-decomposition enzyme is added for performing enzyme reaction. At that time, it is preferable to perform the reaction with stirring.

When the enzyme reaction is performed in the absence of urea and surfactant, after having added chitin-containing material to the solution of urea and/or surfactant, or after having heated the solution hereof, chitin-containing material is washed by water several times, resuspended in buffer solution, and then enzyme is added for enzyme reaction. This method allows the use of such enzymes that are likely to be inactivated by urea. As the buffer solution, buffers usable at the neutral zone are preferable. For this purpose, phosphate buffer, acetate buffer, tris-hydrochloride buffer, etc. are cited, which are prepared to be around neutral in pH.

The temperature for enzyme reaction can be within the temperature range which does not cause the inactivation of enzyme, and is preferably within the range of optimum temperature for the enzyme activity. In case of lysozyme, for instance, the reaction is preferably performed at 30°-60° C.

When chitin-containing material is heated in the solution of urea and/or surfactant, it is possible to perform enzyme reaction concurrent with the denaturing treatment on chitin-containing material, thus shortening the treatment time. In addition, performing the reaction at high temperature can further shorten the treatment time as a result of the acceleration in reaction rate, and produce advantages to prevent the contamination by miscellaneous fungi, etc.

Enzyme reaction can be achieved under the condition of dissolving enzyme in solvent, but can also be performed by utilizing the insoluble carriers fixed with enzyme. The fixation of enzyme can be achieved by the method generally employed, such as, the method used to include enzyme in the polyacrylamide gel, etc, and to make enzyme adsorbed by ion exchange resin.

The purification of the decomposed substance produced from chitin-containing material can be achieved by liquid chromatography, gel filtration, etc.

The method of this invention can be applied similarly to the enzymatic decomposition of both chitosan and chitin, in which case Chitosanase, etc., may be used as enzymes. In addition, the method may be applied to such polysaccharides as cellulose, xylan, other hemicellulose, insoluble protein, etc. which are hard to perform enzyme decomposition efficiently due to their stable three-dimentional structure, or to such polymer compound as lignin, etc. which is hard to decompose. When it is not known whether the enzyme is useable in the presence of urea, the method of performing enzyme reaction after having removed urea, which is described in this invention, can be applied.

DETAILED DESCRIPTION OF THE PREFERRED EMBODIMENTS

Figure 1:
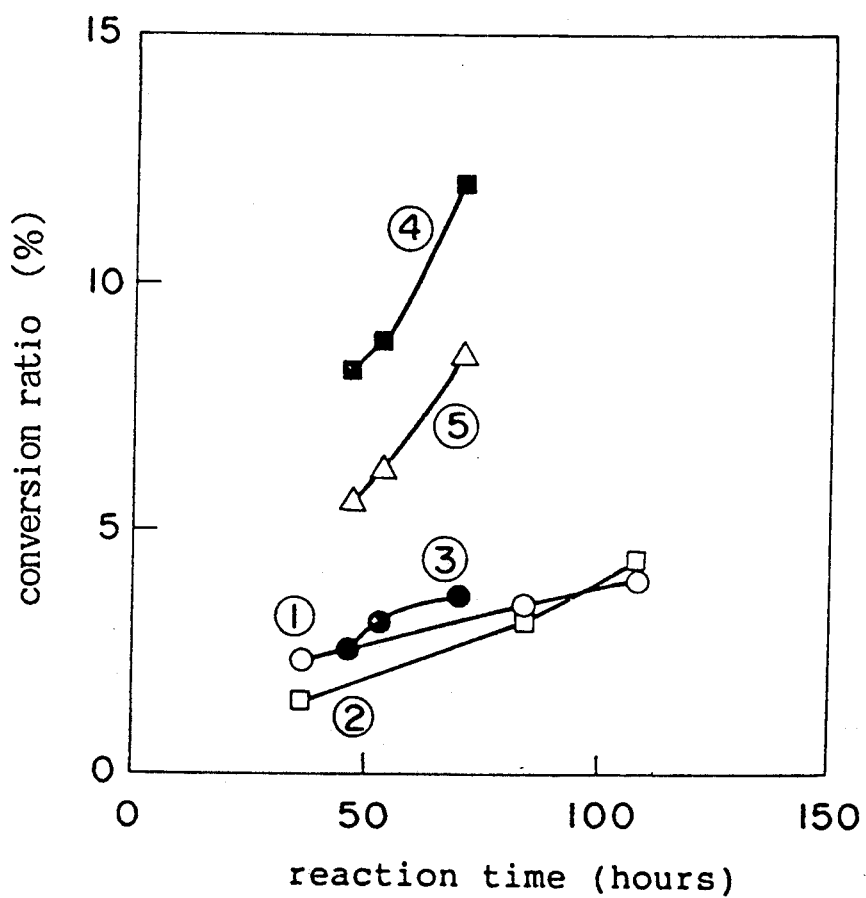
FIG. 1 is a graph which compares the decomposition rate of chitin owing to the difference in solvents.

Embodiments of Nos. 1-6 are concerned with the first method of the present invention; embodiments of Nos. 7-11 are concerned with the second method of the present invention.

EMBODIMENT 1

First of all, improvement in the reactivity of decomposition enzyme was studied by heat-treating chitin in the solvents containing hydrophobic organic solvent.

The reactivity of chitin (Wako Junyaku Kogyo, for biochemistry use) pre-treated under the following 5 conditions was studied against lysozyme.

(1) one in which 0.2 g of chitin is added to 10 ml of 50 mM acetate buffer (pH 5.0)
(2) one in which 0.04 g of chitin is added to the solution prepared by mixing 2 ml of 50 mM acetate buffer (pH 5.0) with 8 ml of dodecane
(3) one which is boiled with stirring for one hour after having added 0.2 g of chitin to 10 ml of 50 mM acetate buffer (pH 5.0)
(4) one which is boiled with stirring for one hour after having added 0.04 g of chitin to the solution prepared by mixing 2 ml of 50 mM acetate buffer (pH 5.0) with 8 ml of dodecane
(5) one in which 2 ml of 50 mM acetate buffer (pH 5.0) is added after having boiled the mixture of 8 ml of dodecane with 0.04 g of chitin for one hour with stirring Out of these substrate solutions, to the solutions of water base, i.e. (1) and (3), 0.2 g of egg white lysozyme (Wako Junyaku Kogyo, No. 122-02673) was added to the solutions of organic solvent base, i.e. (2), (3), and (5), 0.04 g of egg white lysozyme was added. Each of these solutions was placed in a reaction vessel of 30 ml capacity, and the reaction was performed with stirring by magnetic stirrer in 40° C. constant bath.

The analysis on the reaction products was performed by high performance liquid chromatography using Asahi Pak NH2P-50 columns (product of Asahi Kasei Kogyo) or YMC-Pack Polyamine columns (product of Yamamura Chemical Research Institute, purchased from YMC).

The conversion ratio corresponding to the reaction time of each reaction solution (corresponding to the volume of chitin added, the ratio of total volume of monomer, dimer and trimer of N-acetylglucosamine produced) is shown in FIG. 1. The conditions described above, (1)–(5), were respectively illustrated by using the following symbols: ○(1), □(2), ●(3), ■(4), ▲(5).

From this result, it is found that the heat treatment in dodecane, especially in dodecane containing water, makes lysozyme easily act on chitin. Further, it is found that buffer alone shows little effectiveness even if heat-treated and that no effectiveness can be expected without heat-treatment even if dodecane is used.

EMBODIMENT 2

Next, the decomposition effectiveness of chitin was studied by varying the concentration of enzyme while keeping the concentration of chitin constant. After 2–8% of chitin was added to the mixture solution of 1 ml of 50 mM acetate buffer (pH 5.0) and 9 ml of dodecane, which was then boiled for one hour with stirring, 0.5–4% of lysozyme was added. The enzyme reaction was performed in the same way as in Embodiment 1, and the decomposed product was analyzed. Each reaction condition is shown in Table 1.

TABLE 1

| Symbol | Enzyme Concentration | Chitin Concentration |
|---|---|---|
| 1 ○ | 0.5% | 2.0% |
| 2 ● | 1.0% | 2.0% |
| 3 □ | 2.0% | 2.0% |
| 4 ■ | 4.0% | 2.0% |
| 5 △ | 4.0% | 4.0% |
| 6 ▽ | 4.0% | 8.0% |
| 7 ▲ | 2.0% | 2.0%(dodecane 0%) |

Figure 2:
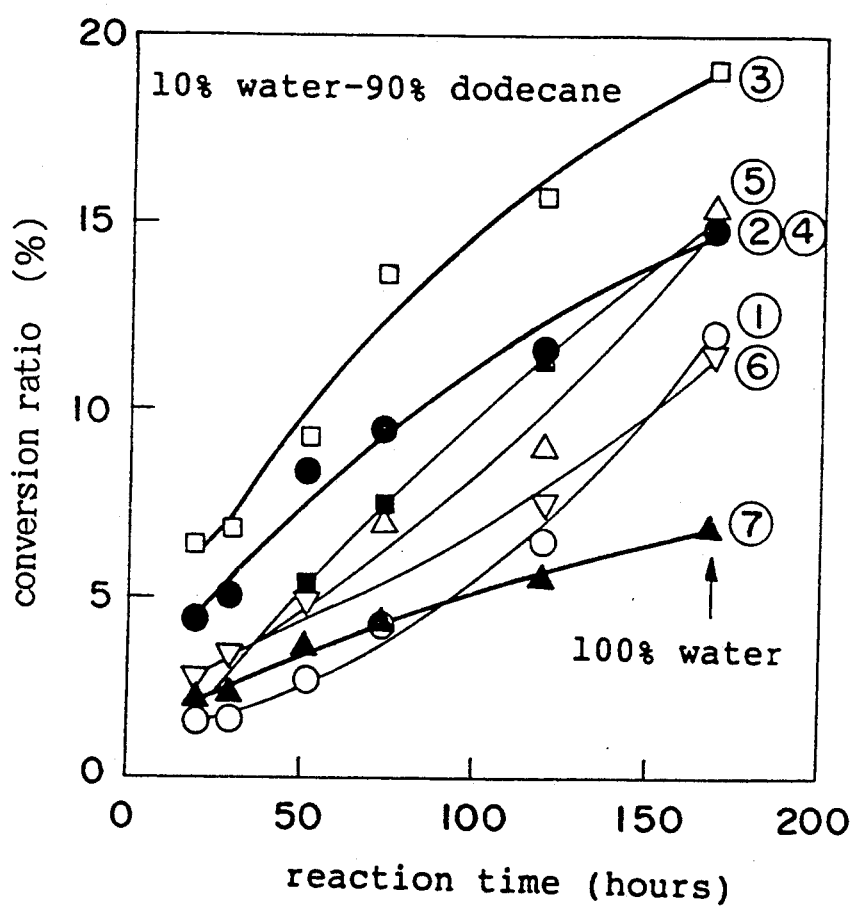
FIG. 2 is a graph which compares the decomposition ratio of chitin owing to the difference in enzyme concentration and substrate concentration.
Figure 3:
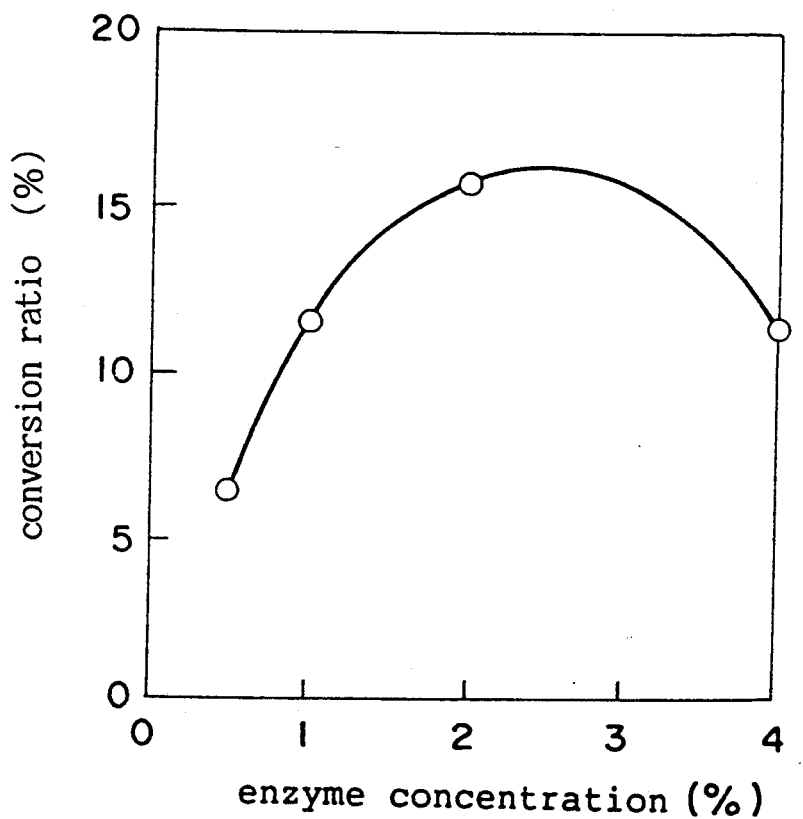
FIG. 3 is a graph which shows the decomposition ratio of chitin against enzyme concentration.

The decomposition rate corresponding to each reaction time is shown in FIG. 2; the decomposition rate corresponding to the concentration of enzyme (concentration of chitin: 2% and reaction time: 120 hours) is shown in FIG. 3. From this result, it is found that, in the solvent in which the ratio of buffer to dodecane is 1:9, the highest decomposition rate is obtained when the concentration of both chitin and enzyme is 2(W/V)%.

EMBODIMENT 3

Figure 4:
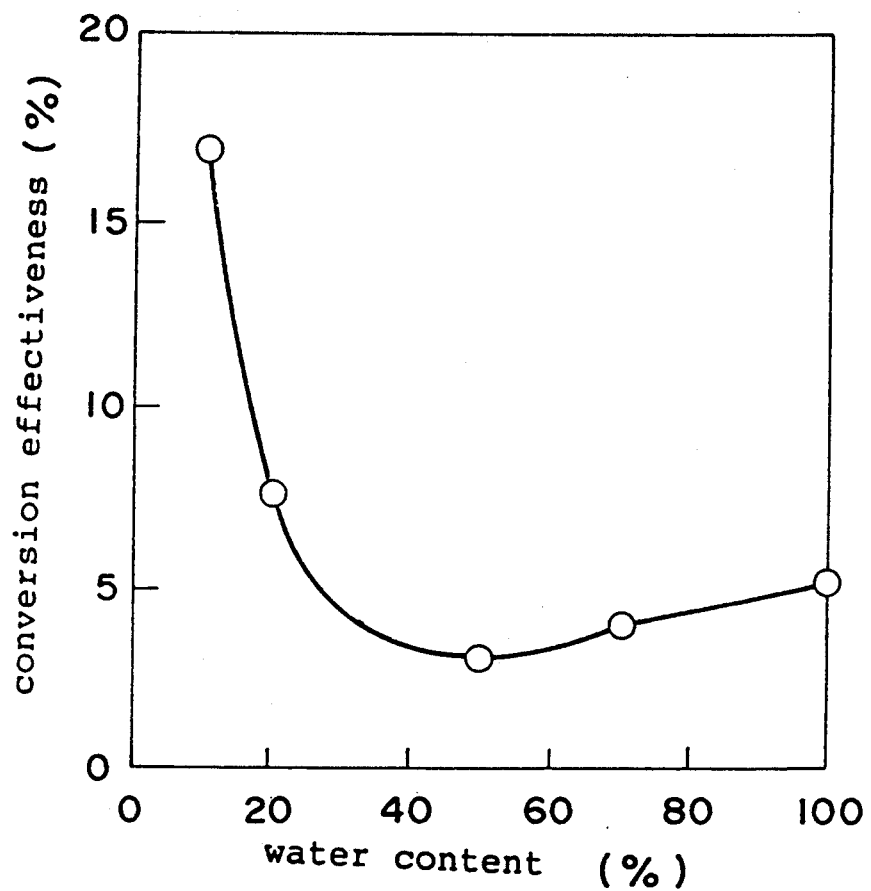
FIG. 4 is a graph which shows the relationship between water content and the decomposition of chitin.

The relationship between the ratio of water contained in the solvent and the decomposition effectiveness of chitin was studied. After chitin was added to the solution of various ratio of dodecane and 50 mM acetate buffer (pH an autoclave, 1 atm to a concentration of 2(W/V)%), 2%(W/V) of lysozyme was added. The reaction was performed in the same way as in embodiment 1, and after 90 hours the decomposed product was analyzed. The result is shown in FIG. 4. From this result, it is found that the ratio of water greatly influences the decomposition effectiveness, and that it is effective when the water content is not more than 30%.

EMBODIMENT 4

The influence of pH on the reaction was studied. After 2(W/V)% of chitin was added to 200 mM acetate buffer (pH 4.0–8.0) or to the mixture of 10% of the same buffer and 90% of dodecane, which was boiled for one hour with stirring, 2(W/V)% of lysozyme was added to perform the reaction at 40° C.

Figure 5:
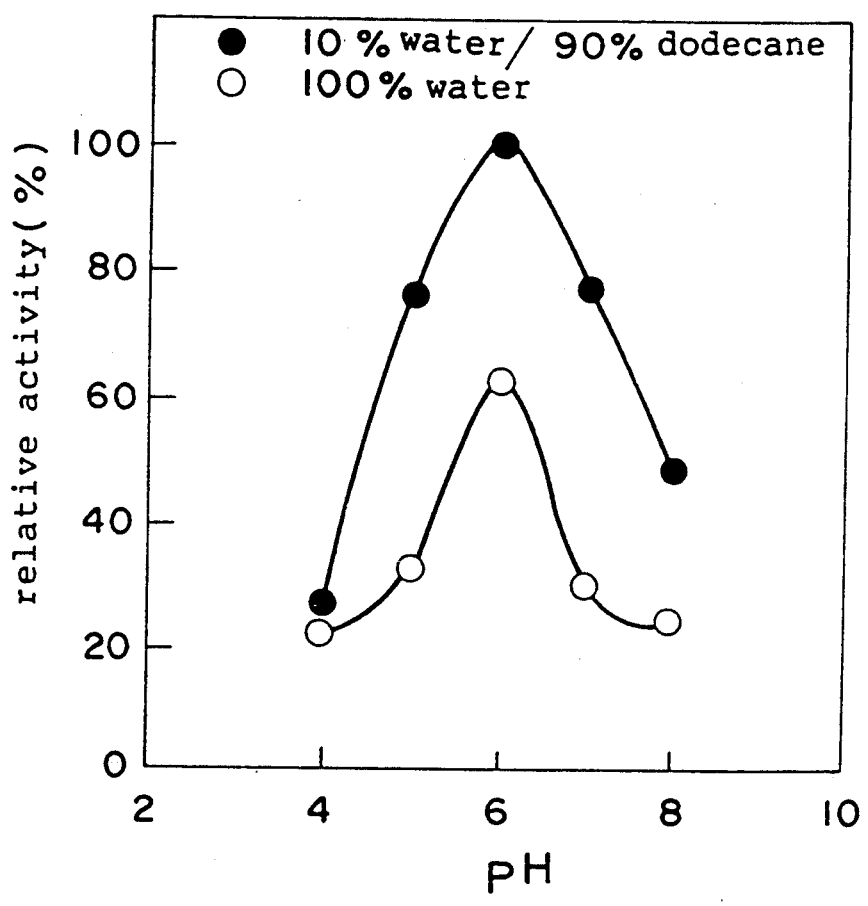
FIG. 5 is a graph which shows the relationship between pH and the decomposition of chitin.

After 90 hours, the total volume of monomer, dimer and trimer of N-acetylglucosamine produced was measured by high performance liquid chromatography. The relative activity corresponding to the activity at pH 6 is shown in FIG. 5. From this result, it is found that the pH at around neutral is effective and suitable.

EMBODIMENT 5

Figure 6:
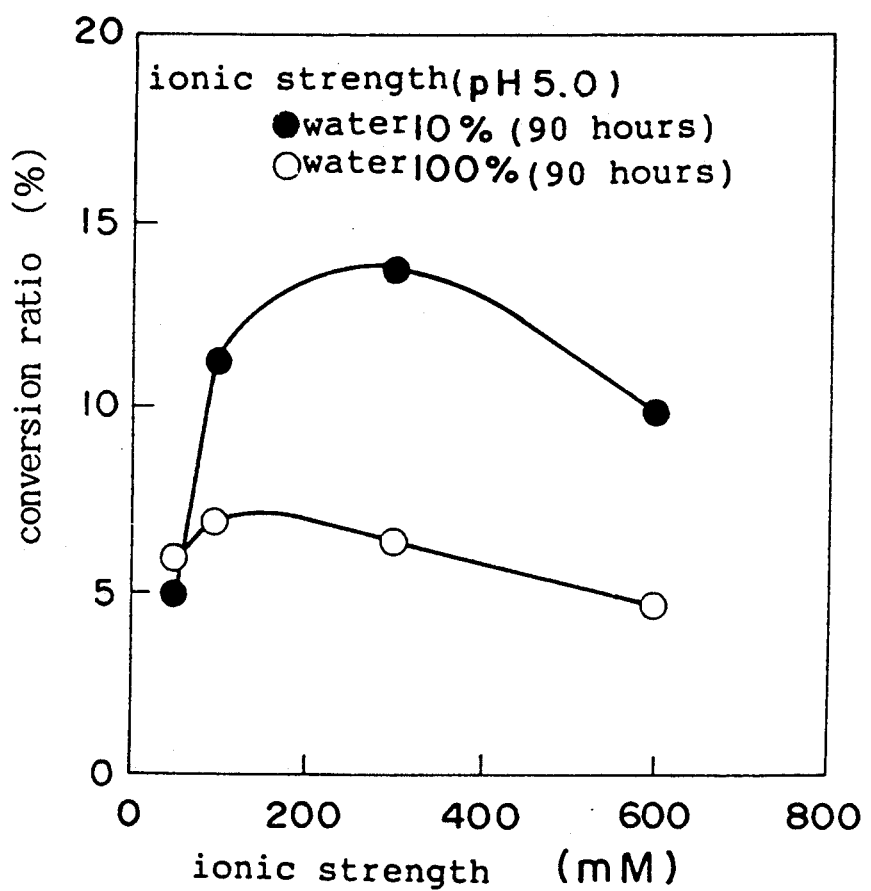
FIG. 6 is a graph which shows the relationship between ionic strength and the decomposition of chitin.

The influence of ionic strength on the reaction was studied by using varying concentration of acetate buffer. In the varying concentration of acetate buffer (pH 5.0) or in the mixture of 10% of the same buffer and 90% of dodecane, 2(W/V)% of chitin was heat-treated by boiling for one hour, which was decomposed by 2(W/V)% of lysozyme at 40° C. The decomposition effectiveness after 90 hours is shown in FIG. 6. From this result, it is found that the ionic strength of buffer solutions is effective and suitable at 100–300 mM in case of water base, and at 100–600 mM in case of water-dodecane base.

EMBODIMENT 6

Figure 7:
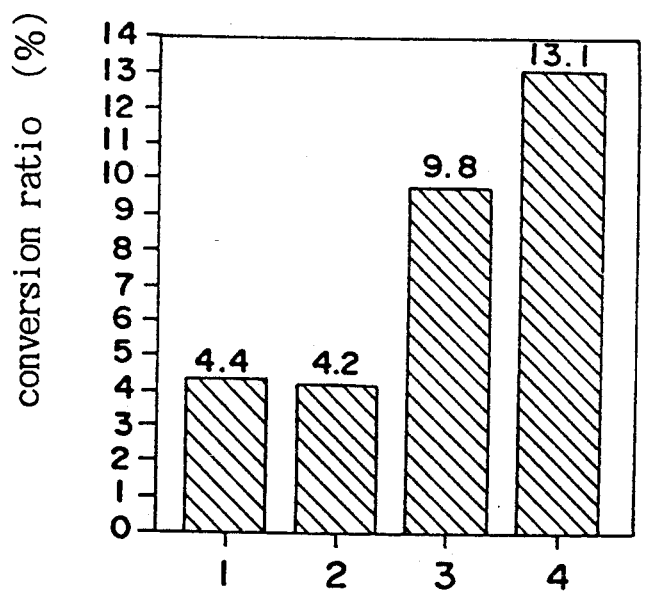
FIG. 7 is a graph which shows the effectiveness of ultrasonication on the decomposition of chitin.

The improvement in reactivity of decomposition enzyme was studied by ultrasonicating chitin in the solvent including hydrophobic organic solvent. After 2(W/V)% of chitin was added to 50 mM acetate buffer (pH 5.0) or to the mixture of 10% of the same buffer and 90% of dodecane, which was ultrasonicated for 5 minutes by using cell-destroying Sonicater (manufactured by Tommy Seiko, Model UR-200P, frequency 20 kHz), 2(W/V)% of lysozyme was added to make it react at 40° C. The conversion ratio after 44 hours was compared among those not heat-treated and those heat-treated for 30 minutes at 100° C. (FIG. 7). Each condition is shown in Table 2.

TABLE 2

| | Ultrasonication | Heat-treatment | Solvent |
|---|---|---|---|
| 1 | x | x | Water |
| 2 | o | x | Water |

TABLE 2-continued

| | Ultrasonication | Heat-treatment | Solvent |
|---|---|---|---|
| 3 | x | o | Water + Dodecane |
| 4 | o | x | Water + Dodecane |

From this result, it is found that the ultrasonication on chitin in organic solvent makes chitin easily decomposed by hydrolysis enzyme, as is the case with heat-treatment.

EMBODIMENT 7

Figure 8:
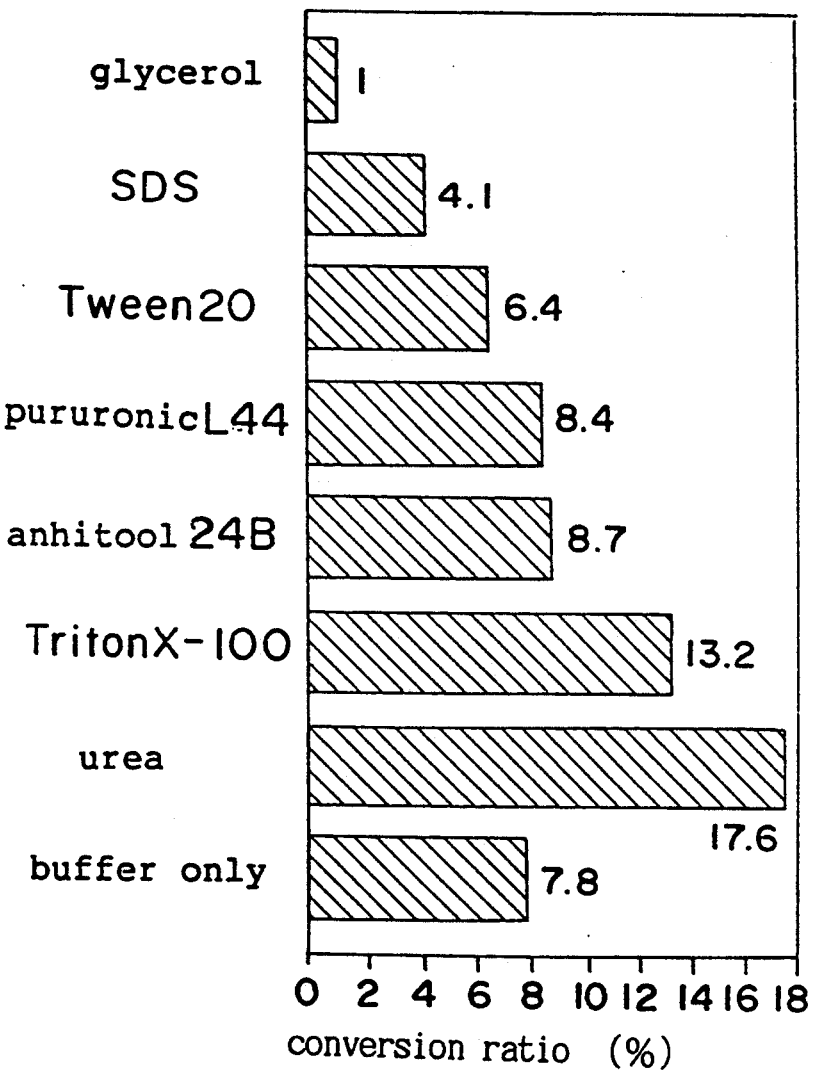
FIG. 8 is a graph which shows the effectiveness of pre-treatment on the decomposition ratio of chitin by chitin decomposition enzyme.

The improvement in the decomposition rate of chitin by chitin decomposition enzyme was studied by means of exposing chitin in the buffer containing urea, etc. After chitin (manufactured by Wako Junyaku Kogyo) was added so as to become 2(W/V)% to 100 mM phosphate buffer (pH 0.6) in which 20(W/V)% glycerol, 0.5(W/V)% SDS (sodium dodecyl sulfate), 1(W/V)% Tween 20, 1(W/V)% Pururonic L44 (manufactured by Asahi Denka), 1(W/V)% Anhitool 24B (manufactured by Kao), Triton X-100 or 0.2M urea are dissolved, of which solution was boiled for one hour at 100° C., lysozyme (manufactured by Wako Junyaku Kogyo, No. 122-02673) was added so as to become 2(W/V)%. The reaction was performed at 40° C. with stirring. The analysis on the reaction product after 41 hours from the start of reaction was performed in the same way as Embodiment 1. The ratio of total volume of monomer, dimer and trimer of N-acetylglucosamine produced by decomposition against the volume of chitin added is shown in FIG. 8 as conversion ratio.

From this result, it is found that the exposure of chitin to the solution containing urea or Triton X-100 makes it easily decomposed by lysozyme.

EMBODIMENT 8

Figure 9:
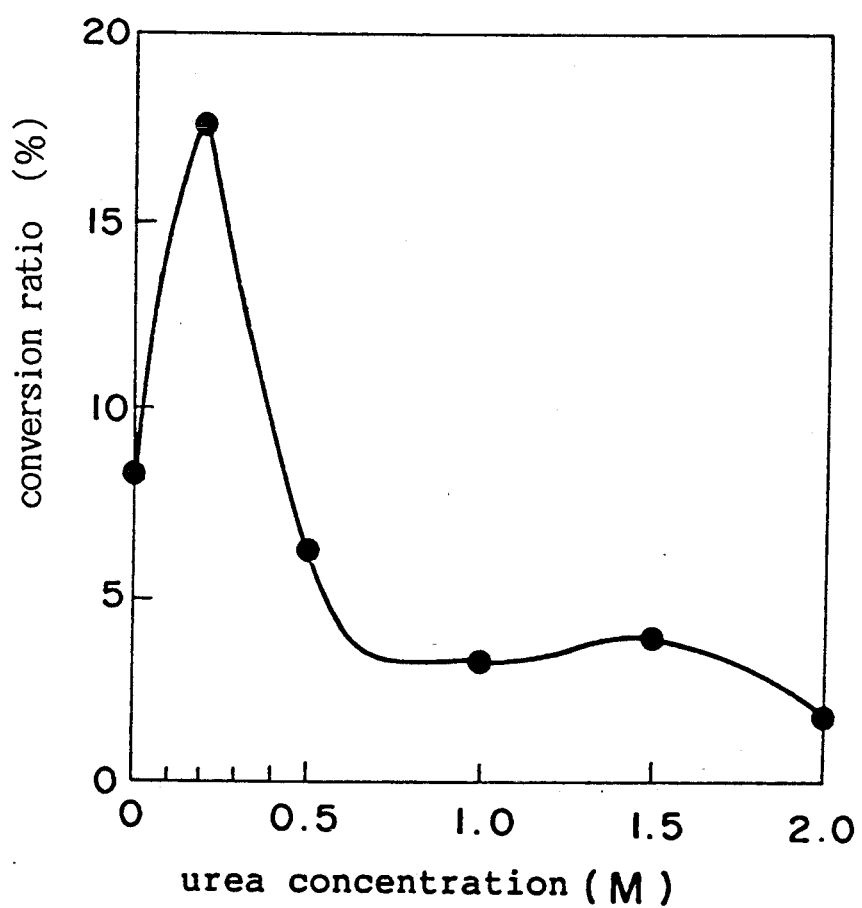
FIG. 9 is a graph which shows the decomposition ratio of chitin and the influence of urea concentration in pre-treatment.

The influence of the concentration of urea on the decomposition of chitin was studied. Chitin (manufactured by Wako Junyaku Kogyo) was added to 100 mM phosphate buffer (pH 6.0) containing 0.2M, 0.5M, 1.0M, 1.5M or 2.0M urea. The decomposition effectiveness was studied in the same way as shown in Embodiment 1, the result of which is shown in FIG. 9. The reaction was performed for 40 hours.

From this result, it is found that the concentration of urea is best at 0.1–0.4M.

EMBODIMENT 9

Figure 10:
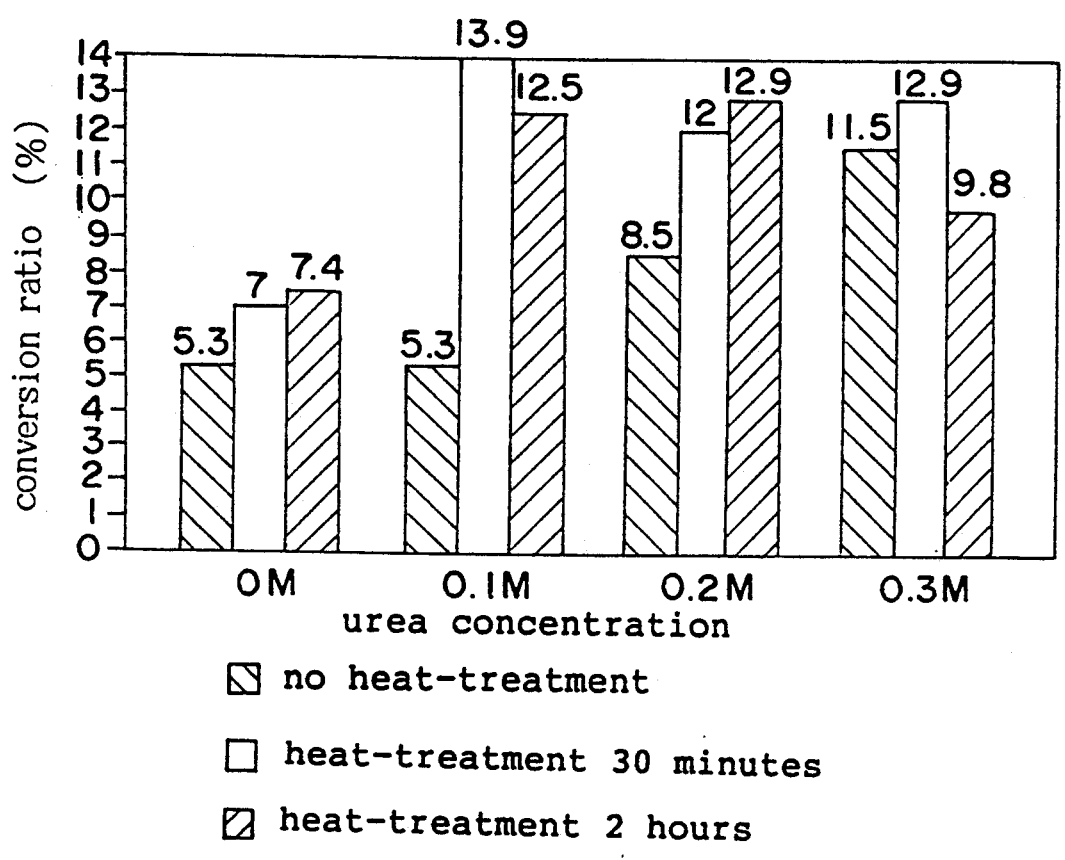
FIG. 10 is a graph which shows the effectiveness of heat-treatment in the pre-treatment on chitin by urea.

The influence of heating at the time of exposing chitin to urea solution on enzymatic decomposition was studied. Chitin (manufactured by Sigma) was added to 100 mM phosphate buffer (pH 6.0) containing urea so as to become 1(W/V)%. To the solution thereof which was heated with stirring for 30 minutes or for 2 hours at 100° C. and to the solution thereof which was not heated, 1(W/V)% lysozyme was added for the reaction at 40° C. The concentration of urea studied was respectively 0.1M, 0.2M and 0.3M. The reaction product was analyzed 67 hours after the addition of enzyme in the same way as shown in Embodiment 1. The conversion ratio is shown in FIG. 10.

From this result, it is found that chitin can be effectively decomposed without heating when the concentration of urea is high, but heating will further heighten the decomposition effectiveness. Especially, the effectiveness of heating is remarkable when urea is low in the concentration.

EMBODIMENT 10

Figure 11:
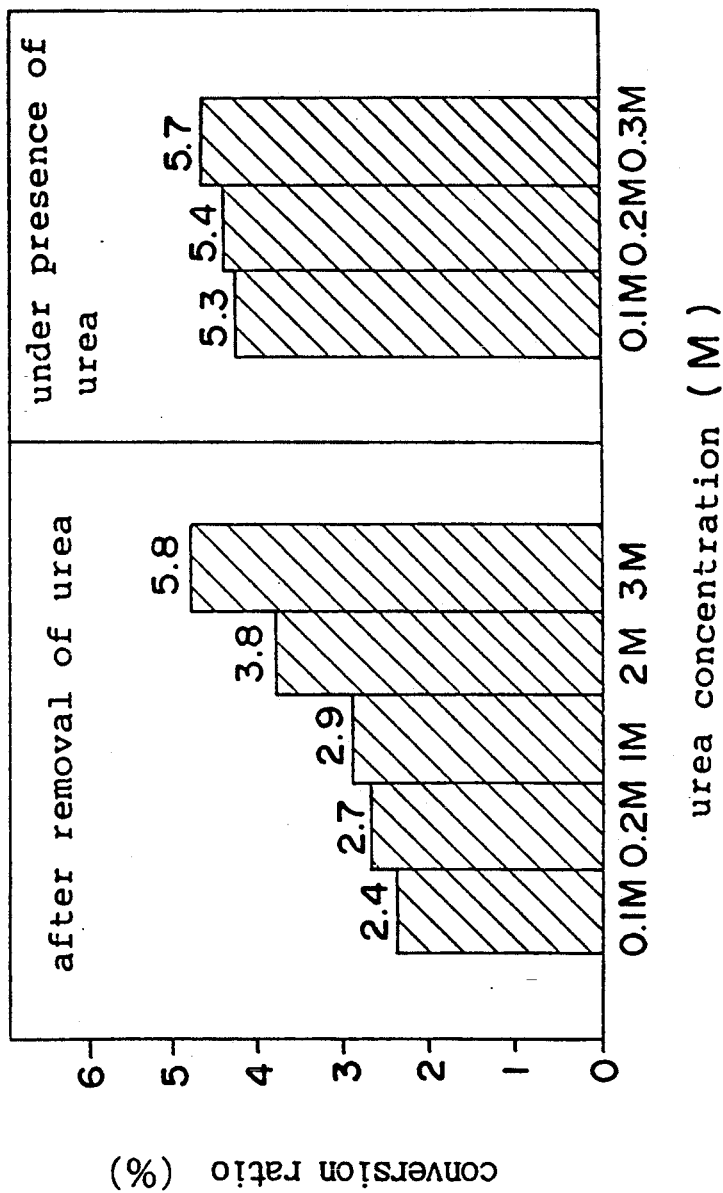
FIG. 11 is a graph which show the influence on the decomposition ratio of chitin given by the presence of urea in enzyme reaction.

Next, the embodiment is described, in which the enzymatic decomposition was performed after having exposed chitin to the urea solution, which was followed by the procedures of washing with water and removing the urea. After 1(W/V)% chitin (manufactured by Sigma) was added to the urea solution, which was heated at 100° C. for 30 minutes with stirring, urea was removed by washing with water several times. The chitin was resuspended in 100 mM phosphate buffer solution (pH 6.0) so as to become 1(W/V)%, to which 1(W/V)% of lysozyme was added for reaction for 42 hours at 40° C. The concentration of urea was respectively 0.1M, 0.2M, 1.0M, 2.0M and 3.0M. The conversion ratio was measured in the same way as shown in Embodiment 1, and compared with that in which the enzymatic decomposition was made under the presence of urea. (FIG. 11)

From the result, it has been found that chitin can be decomposed efficiently even if the enzyme reaction is performed after having removed urea.

EMBODIMENT 11

Figure 12:
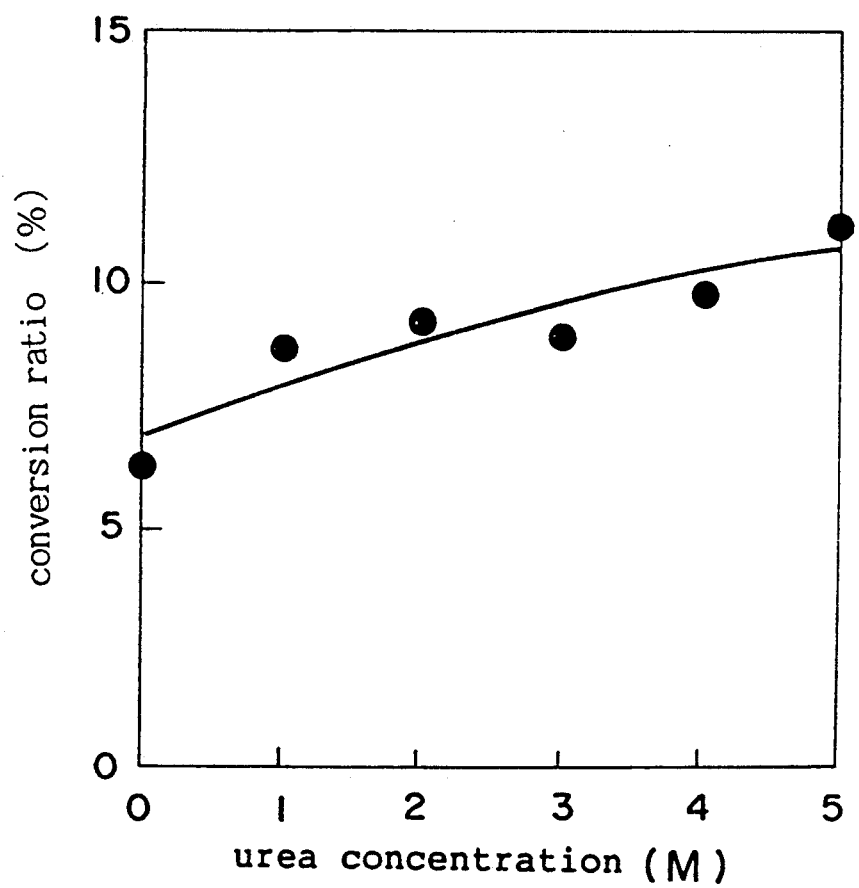
FIG. 12 is a graph which shows the relationship between urea concentration in pre-treatment and the decomposition ratio of chitin in case that enzyme reaction is not performed in the presence of urea.

The Embodiment is described in which chitin was processed in highly concentrated urea solution. To 100 mM phosphate buffer (pH 6.0) containing 0–5M urea, chitin (manufactured by Sigma) is added so as to become 1(W/V)%, which is then stirred for 24 hours at room temperature. After this, urea was removed by washing the chitin. The chitin was suspended in 100 mM phosphate buffer solution (pH 6.0), to which 1(W/V)% lysozyme was added. The reaction was performed with stirring at 40° C. After 96 hours, the reaction product was analyzed in the same way as described in Embodiment 1, and the conversion ratio is shown in FIG. 12.

From this result, it is found that chitin is more easily decomposed in a solution of highly concentrated urea.

What is claimed is:

1. An enzymatic method of decomposing chitin, comprising:
    mixing the chitin with an organic solvent, thereby creating a chitin and solvent mixture, wherein the mixing step comprises ultrasonicating the chitin and solvent mixture;
    heating the chitin and solvent mixture; and
    adding $\beta$-1,4 glycosidase to the mixture.

2. An enzymatic method of decomposing chitin, comprising the steps of:
    soaking the chitin in a solution selected from the group consisting of urea, a surfactant, and a mixture of urea and a surfactant; and
    adding $\beta$-1,4 glycosidase to the chitin.

3. The method of claim 2, further comprising separating the chitin from the solution before adding $\beta$-1,4 glycosidase.

4. The method of claim 2, further comprising heating the chitin in said solution.

5. The method of claim 2, wherein said $\beta$-1,4 glycosidase is selected from the group consisting of lysozyme and chitinase.

6. An enzymatic method of decomposing chitin, comprising:
    mixing the chitin with a hydrophobic organic solvent thereby creating a chitin and solvent which is insoluble in water mixture;
    heating the chitin and solvent mixture; and adding β-1,4 glycosidase to the mixture.

7. The method of claim 6, wherein said organic solvent is mixed with water prior to the mixing step.

8. The method of claim 6, wherein said organic solvent is selected from the group consisting of hexane, heptane, octane, 2-methyl heptane, 2,2,4-trimethyl heptane, nonane, decane, undecane, dodecane, methyl cyclobutane, cyclohexane, methylcyclohexane, benzene, toluene, o-xylene, m-xylene, p-xylene, ethyl benzene, cumene, oil of ligroin, carbon tetrachloride, 1,2-dichloroethane, 1,1,2,2-tetrachloroethane, trichloroethylene, chlorobenzene, and 2,6-dichlorobenzene.

9. The method of claim 6, wherein said β-1,4 glycosidase is selected from the group consisting of lysozyme and chitinase.

10. The method of claim 6, further comprising adding a surfactant.

11. The method of claim 6, wherein said chitin is present in a material selected from the group consisting of the outer shells of Crustaceans, the outer shells of insects and the cell walls of fungi.

* * * * *